United States Patent [19]
Valint, Jr.

[11] 3,948,944
[45] Apr. 6, 1976

[54] O-ETHYL-S-PROPYL DERIVATIVES OF 1,3-DITHIOLAN-4-YL PHOSPHORODITHIOATES-METHYL

[75] Inventor: Paul L. Valint, Jr., Woodbridge, N.J.

[73] Assignee: Exxon Research & Engineering Co., Linden, N.J.

[22] Filed: Jan. 15, 1973

[21] Appl. No.: 323,482

Related U.S. Application Data

[63] Continuation of Ser. No. 41,599, May 28, 1970, abandoned.

[52] U.S. Cl. .............................. 260/327 M; 424/202
[51] Int. Cl. ........................................... C07d 339/06
[58] Field of Search ............................... 260/327 M

[56] References Cited
UNITED STATES PATENTS

| | | | |
|---|---|---|---|
| 2,690,988 | 10/1954 | Jones et al. | 424/277 |
| 3,317,561 | 5/1967 | Levy et al. | 260/327 |

FOREIGN PATENTS OR APPLICATIONS

| | | | |
|---|---|---|---|
| 40-2073 | 2/1965 | Japan | 260/327 |

Primary Examiner—Norma S. Milestone
Assistant Examiner—C. M. S. Jaisle

[57] ABSTRACT

Compounds characterized by the following formula:

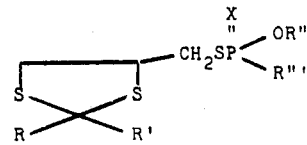

wherein R and R' can be selected from the group consisting of $C_1$ to $C_{15}$ hydrocarbyl, preferably $C_1$ to $C_6$ alkyl, $C_3$ to $C_7$ cycloalkyl, phenyl optionally substituted by chlorine, bromine, nitro, cyano, $C_1$ to $C_6$ alkyl, $C_1$ to $C_6$ alkoxy or $C_1$ to $C_6$ alkylthio; R and R' may form together a carbocyclic ring of from 3 to 8 carbon atoms. In addition, R can also be hydrogen. R'' can be a $C_1$ to $C_6$ alkyl group optionally substituted by chlorine, bromine or cyano; phenyl optionally substituted by chlorine, bromine or nitro, R''' can have the same definition as R'' and can be in addition a $C_1$ to $C_6$ alkoxy, $C_1$ to $C_4$ alkylthio and phenoxy optionally substituted by chlorine, bromine or nitro; X can be oxygen or sulfur.

These compounds have been found to possess pesticidal activity, particularly insecticidal, miticidal and nematocidal activity.

3 Claims, No Drawings

O-ETHYL-S-PROPYL DERIVATIVES OF 1,3-DITHIOLAN-4-YL PHOSPHORODITHIOATES-METHYL

This is a continuation of application Ser. No. 41,599, filed on May 28, 1970, now abandoned.

This invention relates to derivatives of 1,3-dithiolanes. One aspect of this invention relates to novel thiophosphate derivatives of 1,3-dithiolanes. In another aspect this invention relates to the use of such derivatives for insecticidal and miticidal purposes.

Under the prior art, an Australian Pat. No. 36566/63 assigned to American Cyanamide Company describes organophosphorus derivatives of dithiolanes characterized by the following generic formula;

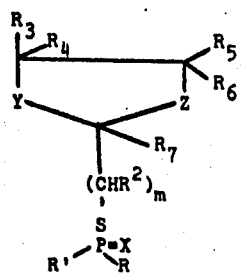

wherein R and R' are alkyl, phenyl, alkoxy, alkylthio, alkylamino; $R_2$ to $R_7$ are hydrogen, lower alkyl, lower carbylalkoxy, halo, lower alkyl, phenyl, substituted phenyl, benzyl radicals; X is O or S; and Y and Z are O, $S(O)_n$; and $n$ equals 0 – 2 and $m$ equals 1 or 2.

The compounds of the subject invention differ from those in the Australian patent in that the organophosphorus moiety is not located between the two heteroatoms.

In addition, the Farbenfabriken Bayer Company has filed an application in Belgium, Ser. No. 737,721, published in Germany on Feb. 2, 1970, which discloses compounds having the following structures:

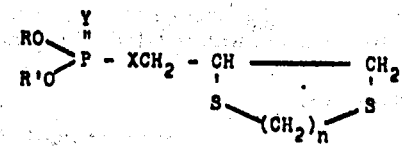

wherein R and R' are $C_1$-$C_6$ alkyl; X and Y are either O or S; $n = 1$ or 2.

The difference between these compounds and those being claimed in the subject application is that there is no substitution occurring on the methylene groups located between the two sulfur atoms. In the subject compounds there must be at least one substituent on the methylene group.

Another difference is that some of the compounds in the subject application are the O → S isomers of the compound disclosed in the aforesaid Belgian application. Such O → S isomers have been found to possess Southern Armyworm activity.

The compounds characterized by the subject invention have the following formula:

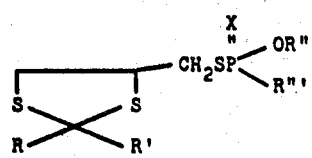

wherein R and R' can be selected from the group consisting of $C_1$ to $C_{15}$ hydrocarbyl, preferably $C_1$ to $C_6$ alkyl, $C_3$ to $C_7$ cycloalkyl, phenyl optionally substituted by chlorine, bromine, nitro, cyano, $C_1$ to $C_6$ alkyl, $C_1$ to $C_6$ alkoxy or $C_1$ to $C_6$ alkylthio; R and R' may form together a carbocyclic ring of from 3 to 8 carbon atoms. In addition, R can also be hydrogen. R'' can be a $C_1$ to $C_6$ alkyl group optionally substituted by chlorine, bromine or cyano; phenyl optionally substituted by chlorine, bromine or nitro; R''' can have the same definition as R'' and can be in addition a $C_1$ to $C_6$ alkoxy, $C_1$ to $C_4$ alkylthio and phenoxy optionally substituted by chlorine, bromine or nitro; X can be oxygen or sulfur.

These compounds have been found to possess pesticidal activity, particularly insecticidal, miticidal and nematocidal activity.

Specific examples of the organic phosphorus derivatives of the 1,3-dithiolanes of the subject invention which are encompassed within the above generic formula are the following:

| Compound No. | |
|---|---|
| 1 | O,O-diethyl S-[(2-methyl 1,3-dithiolan-4-yl)methyl] phosphorothioate |
| 2 | O,O-diethyl S-[(2-methyl 1,3-dithiolan-4-yl)methyl] phosphorodithioate |
| 3 | O-ethyl S-1-propyl S'-[(2-methyl 1,3-dithiolan-4-yl) methyl] phosphorodithioate |
| 4 | O,O-dimethyl S-[(2,2-dimethyl 1,3-dithiolan-4-yl) methyl] phosphorothioate |
| 5 | O,O-dimethyl S-[(2,2-dimethyl 1,3-dithiolan-4-yl) methyl] phosphorodithioate |
| 6 | O,O-diethyl-S-[(2,2-dimethyl-1,3-dithiolan-4-yl)-methyl]phosphorothioate |
| 7 | O,O-diethyl S-[(2,2-dimethyl 1,3-dithiolan-4-yl) methyl] phosphorodithioate |
| 8 | O-ethyl S-1-propyl S'-[(2,2-dimethyl 1,3-dithiolan-4-yl) methyl] phosphorodithioate |
| 9 | O,O-dimethyl S-[(2-butyl 2-methyl 1,3-dithiolan-4-yl) methyl] phosphorothioate |
| 10 | O,O-diethyl S-[(2-butyl 2-methyl 1,3-dithiolan-4-yl) methyl] phosphorodithioate |
| 11 | O,S-diethyl S-[(2-methyl 2-propyl 1,3-dithiolan-4-yl) methyl] phosphorodithioate |
| 12 | O,O-dimethyl S-[(2-cyclopropyl 2-methyl 1,3-dithiolan- |

13  O,O-dipropyl S-[(2-cyclopropyl 2-methyl 1,3-dithiolan-4-yl) methyl]phosphorodithioate
14  O,O-diethyl S-[(2-cyclohexyl 2-ethyl 1,3-dithiolan-4-yl) methyl] phosphorothioate
15  O-ethyl S-1-propyl S-[(2-cyclohexyl 2-ethyl 1,3-dithiolan-4-yl) methyl] phosphorodithioate
16  O,O-dimethyl-S-[(2,2-dicyclopentyl 1,3-dithiolan-4-yl) methyl] phosphorodithioate
17  O,O-dipropyl-S-[(2,2-dicyclopentyl 1,3-dithiolan-4-yl) methyl] phosphorothioate
18  O-ethyl S-1-propyl S'-[(2,2-dicyclohexyl 1,3-dithiolan-4-yl) methyl] phosphorodithioate
19  O,O-dimethyl S-[(2-phenyl 1,3-dithiolan-4-yl) methyl] phosphorothioate
20  O,O-dimethyl S-[(2-phenyl 1,3-dithiolan-4-yl) methyl] phosphorodithioate
21  O,O-diethyl S-[(2-phenyl 1,3-dithiolan-4-yl) methyl] phosphorothioate
22  O,O-diethyl S'-[(2-phenyl 1,3-dithiolan-4-yl) methyl] phosphorodithioate
23  O-ethyl S-1-propyl S-[(2-phenyl 1,3-dithiolan-4-yl) methyl] phosphorodithioate
24  O,O-dimethyl S-{[2-(4-chlorophenyl) 1,3-dithiolan-4-yl] methyl} phosphorothioate
25  O,O-diethyl S-{[2-(4-nitrophenyl) 1,3-dithiolan-4-yl] methyl} phosphorodithioate
26  O,S-diethyl S'-{[2-(4-methoxyphenyl) 1,3-dithiolan-4-yl] methyl} phosphorodithioate
27  O,O-dipropyl S-[(2-methyl 2-phenyl 1,3-dithiolan-4-yl) methyl] phosphorothioate
28  O-ethyl S-1-propyl S'-[(2-cyclopropyl 2-tolyl 1,3-dithiolan-4-yl) methyl] phosphorodithioate
29  O,O-dimethyl S-[(2,2-spirocyclopentyl 1,3-dithiolan-4-yl) methyl] phosphorothioate
30  O,O-dimethyl S-[(2,2-spirocyclopentyl 1,3-dithiolan-4-yl) methyl] phosphorodithioate
31  O,O-diethyl S-[(2,2-spirocyclopentyl 1,3-dithiolan-4-yl) methyl] phosphorothioate
32  O,O-diethyl S-[(2,2-spirocyclopentyl 1,3-dithiolan-4-yl) methyl] phosphorothioate
33  O,ethyl S-1-propyl S'-[(2,2-spirocyclopentyl 1,3-dithiolan-4-yl) methyl] phosphorodithioate The preparation of the 4-chloromethyl 1,3-dithiolane precursors of the claimed compounds has been described by Roberts and Cheng [J. Org. Chem., 23, 983(1958)].

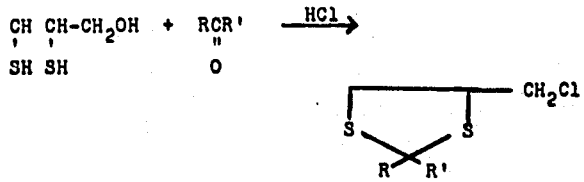

However, when 2-phenyl or 2,2-spirocyclopentyl substituents of the 1,3-dithiolane ring are required, the desired 4-chloromethyl compounds were prepared by a second route which involves the preparation of 4-hydroxymethyl derivatives and subsequent conversion to the 4-bromomethyl derivatives by treatment with phosphorus tribromide, according to the following schematic equation:

Reaction (A):

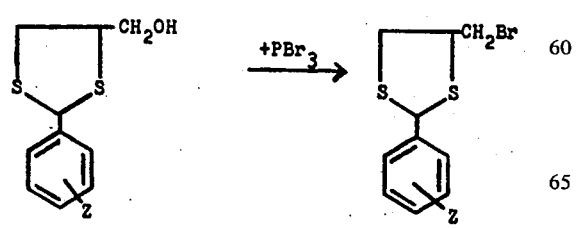

where Z can be chlorine, bromine, nitro, cyano, alkyl, alkoxy or alkylthio

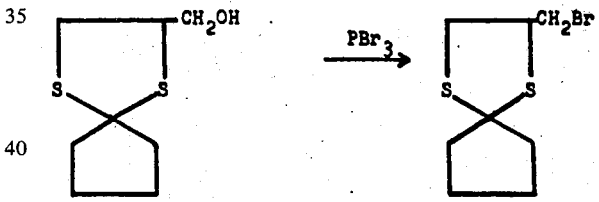

Conversion of the 4-halomethyl derivatives to phosphates involves reaction with the desired organophosphate salt.

Reaction (B):

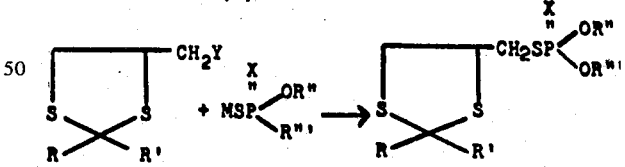

Y = Cl or Br; M = Na, K or NH$_4$

In Reaction (A), the phosphorus tribromide is employed in excess in the presence of an aprotic solvent such as diethyl ether, benzene or chloroform. The reaction temperature can vary between −20°C. and 100°C. preferably between 0°C. and 30°C. The pressure employed is usually atmospheric. The reaction times can vary from 4 hours to 48 hours, preferably 10 hours to 20 hours. The desired product is isolated for further reaction to yield phosphate esters.

In the conversion of the 4-halomethyl 1,3-dithiolanes to phsophate ester derivatives Reaction (B) equal moles of all the reactants were utilized. Displacement reaction can be carried out with or without a solvent. However, it is usually advantageous to use a solvent which can be a polar organic compound such as nitriles, ketones, alcohols, etc. Hydrocarbons and their chlorinated derivatives such as xylenes, chlorobenzene, etc. are also suitable. The preferred solvents for this displacement reaction are either acetonitrile or acetone.

The reaction temperatures can vary from about 0°C. to 150°C, preferably from about 25°C. to 120°C. The pressure of the reactions is usually atmospheric.

Reaction times can vary from 1 to 48 hours, preferably from about 2 to 12 hours.

Insecticidal compositions of the invention are prepared by admixing one or more of the active ingredients defined heretofore, in insecticidally effective amounts with a conditioning agent of the kind used and referred to in the art as a pest control adjuvant or modifier to provide formulations adapted for ready and efficient application to soil or crops using conventional applicator equipment.

Thus, the insecticidal compositions or formulations are prepared in the form of solids or liquids. Solid compositions are preferably in the form of granulars or dusts.

The compositions can be compounded to give homogenous free-flowing dusts by admixing the active compound or compounds with finely divided solids preferably talc, natural clays, pyrophyllite, diatomaceous earth, or flours such as walnut shell, wheat, redwood, soya bean, and cottonseed flours. Other inert solid conditioning agents or carriers of the kind conventionally employed in preparing pest control compositions in powdered form can be used.

Granulars can be compounded by absorbing the compound in liquid form onto a preformed granular diluent. Such diluents as natural clays, pyrophyllite, diatomaceous earth, flours such as walnut shell, as well as granular sand can be employed.

In addition, granulars can also be compounded by admixing the active ingredient with one of the powdered diluents described hereinabove, followed by the step of either pelleting or extruding the mixture.

Liquid compositions of the invention are prepared in the usual way by admixing one or more of the active ingredient with a suitable liquid diluent medium. In the cases where the compounds are liquids, they may be sprayed in ultra low volume as such. With certain solvents, such as alkylated naphthalene or other aromatic petroleum solvents, dimethyl formamide, cycloketone, relatively high up to about 50% by weight or more concentration of the active ingredient can be obtained in solution.

The insecticidal compositions of the invention whether in the form of dusts or liquids, preferably also include a surface-active agent sometimes referred to in the art as a wetting, dispersing, or emulsifying agent. These agents, which will be referred to hereinafter more simply as surface-active dispersing agents, cause the compositions to be easily dispersed in water to give aqueous sprays which, for the most part, constitute a desirable composition for application.

The surface-active dispersing agents employed can be of the anionic, cationic, or nonionic type and include, for example, sodium and potassium oleate, the amine salts of oleic acid, such as morpholine and dimethylamine oleates, the sulfonated animal and vegetable oils, such as sulfonated fish and castor oils, sulfonated petroleum oils, sulfonated acyclic hydrocarbons, sodium salt of lignin sulfonic acid (goulac), alkylnaphthalene sodium sulfonate, sodium salts of sulfonated condensation products of naphthalene and formaldehyde, sodium lauryl sulfate, disodium monolauryl phosphate, sorbitol laurate, pentaerythritol monostearate, glycerol monostearate, diglycol oleate, polyethylene oxides, ethylene oxide condensation products with steryl alcohol and alkylphenol, polyvinyl alcohols, salts, such as the acetate of polyamines from reductive amination of ethylene/carbon monoxide polymers, laurylamine hydrochloride, laurylpyridinium bromide, stearyl trimethylammonium bromide, cetyldimethylbenzyl ammonium chloride, lauryldimethylamine oxide, and the like. Generally, the surface-active agent will not comprise more than about 5 to 15% by weight of the composition, and in certain compositions the percentage will be 1% or less. Usually, the minimum lower concentration will be 0.1%.

The active compound is, of course, applied in an amount sufficient to exert the desired insecticidal action. The amount of the active compound present in the compositions as actually applied for controlling insects will vary with the manner of application, the particular insects for which control is sought, the purpose for which the application is being made, and like variables. In general, the insecticidal compositions as applied in the form of a spray, dust or granular, will contain from about 0.1% to 100% by weight of the active compound.

The term "carrier" or "diluent" as used herein means a material, which can be inorganic or organic and synthetic or of natural origin, with which the active ingredient is mixed or formulated to facilitate its storage, transport, and handling and application to the plants to be treated. The carrier is preferably biologically and chemically inert and, as used, can be a solid or fluid. When solid carriers are used, they are preferably particulate, granular, or pelleted; however, other shapes and sizes of solid carrier can be employed as well. Such preferable solid carriers can be natural occurring minerals — although subsequently subjected to grinding, sieving, purification, and/or other treatments — including, for example, gypsum; tripolite; diatomaceous earth; mineral silicates such as mica, vermiculite, talc, and pyrophyllite; clays of the montmorillonite; keolinite, or attapulgite groups; calcium or magnesium limes, or calcite and dolomite; etc. Carriers produced synthetically, as for example, synthetic hydrated silica oxides and synthetic calcium silicates can also be used, and many proprietary products of this type are available commercially. The carrier can also be an elemental substance such as sulfur or carbon, preferably an activated carbon. If the carrier possesses intrinsic catalytic activity such that it would decompose the active ingredient, it is advantageous to incorporate a stabilizing agent, as for example, polyglycols such as diethylene glycol, to neutralize this activity and thereby prevent possible decomposition of the present compounds.

For some purposes, a resinous or waxy carrier can be used, preferably one which is solvent soluble or thermoplastic, including fusible. Examples of such carriers are natural or synthetic resins such as a coumarone resin, rosin, copal, shellac, dammer, polyvinyl chloride, styrene polymers and copolymers, a solid grade of polychlorophenol such as is available under the registered trademark "Aroclor," a bitumen, an asphaltite, a wax for example, beeswax or a mineral wax such as paraffin wax or montan wax, or a chlorinated mineral wax, or a microcrystalline wax such as those available under the registered trademark "Mikrovan Wax." Compositions comprising such resinous or waxy carriers are preferably in granular or pelleted form.

Fluid carriers can be liquids, as for example, water, or an organic fluid, including a liquefied normally vaporous or gaseous material, or a vaporous or gaseous material, and can be solvents or nonsolvents for the active material. For example, the horticultural petroleum spray oils boiling in the range of from about 275° to about 575°F., or boiling in the range of about 575° to about 1,000°F. and having an unsulfonatable residue of at least about 75% and preferably of at least about 90%, or mixtures of these two types of oil, are particularly suitable liquid carriers.

The carrier can be mixed or formulated with the active material during its manufacture or at any stage subsequently. The carrier can be mixed or formulated with the active material in any proportion depending on the nature of the carrier. One or more carriers, moreover, can be used in combination.

The compositions of this invention can be concentrates, suitable for storage or transport and containing, for example, from about 5 to about 90% by weight of the active ingredient, preferably from about 20 to about 80 wt. %. These concentrates can be diluted with the same or different carrier to a concentration suitable for application. The compositions of this invention may also be dilute compositions suitable for application. In general, concentrations of about 0.1 to about 10% by weight, of active material based on the total weight of the composition are satisfactory, although lower and higher concentrations can be applied if necessary.

The compositions of this invention can also be formulated as dusts. These comprise an intimate admixture of the active ingredient and a finely powdered solid carrier such as aforedescribed. The powdered carriers can be oiltreated to improve adhesion to the surface to which they are applied. These dusts can be concentrates, in which case a highly sorptive carrier is preferably used. These require dilution with the same or a different finely powdered carrier, which can be of lower sorptive capacity, to a concentration suitable for application.

The compositions of the invention can be formulated as wettable powders comprising a major proportion of the active ingredient mixed with a dispersing, i.e. deflocculating or suspending agent, and if desired, a finely divided solid carrier and/or a wetting agent. The active ingredient can be in particulate form or adsorbed on the carrier and preferably constitutes at least about 10%, more preferably at least about 25%, by weight of the composition. The concentration of the dispersing agent should in general be between about 0.5 and about 5% by weight of the total composition, although larger or smaller amounts can be used if desired.

The dispersing agent used in the composition of this invention can be any substance having definite dispersing, i.e., deflocculating or suspending, properties as distinct from wetting properties, although these substances can also possess wetting properties as well.

The dispersant or dispersing agent used can be protective colloids such as gelatin, glue, casein, gums, or a synthetic polymeric material such as polyvinyl alcohol and methyl cellulose. Preferably, however, the dispersants or dispersing agents used are sodium or calcium salts of high molecular weight sulfonic acids, as for example, the sodium or calcium salts of lignin sulfonic acids derived from sulfite cellulose waste liquors. The calcium or sodium salts of condensed aryl sulfonic acid, for example, the products known as "Tamol 731," are also suitable.

The wetting agents used can be nonionic type surfactants, as for example, the condensation products of fatty acids containing at least 12, preferably 16 to 20, carbon atoms in the molecule, or abietic acid or naphthenic acid obtained in the refining of petroleum lubricating oil fractions with alkylene oxides such as ethylene oxide or propylene oxide, or with both ethylene oxide and propylene oxide, as for example, the condensation product of oleic acid and ethylene oxide containing about 6 to 15 ethylene oxide units in the molecule. Other nonionic wetting agents like polyalkylene oxide polymers, commercially known as "Pluronics" can be used. partial esters of the above acids with polyhydric alcohols such as glycerol, sorbitol, or mannitol can also be used.

Suitable anionic wetting agents include the alkali metal salts, preferably sodium salts, of surfuric acid esters or sulfonic acids containing at least 10 carbon atoms in a molecule, for example, the sodium secondary alkyl sulfates, dialkyl sodium sulfosuccinate available under the registered trademark "Teepol," sodium salts of sulfonated castor oil, sodium dodecyl benzene sulfonate.

Granulated or pelleted compositions comprising a suitable carrier having the active ingredient incorporated therein are also included in this invention. These can be prepared by impregnating a granular carrier with a solution of the inert ingredient or by granulating a mixture of a finely divided solid carrier and the active ingredient. The carrier used can consist of or contain a fertilizer or fertilizer mixture, as for example, a superphosphate.

The compositions of this invention can also be formulated as solutions of the active ingredient in an organic solvent or mixture of solvents, such as for example, alcohols; ketones, especially acetone; ethers; hydrocarbons; etc.

Where the toxicant itself is a liquid these materials can be sprayed on crops or insects without further dilution.

Petroleum hydrocarbon fractions used as solvents should preferably have a flash point above 73°F., an example of this being a refined aromatic extract of kerosene. Auxiliary solvents such as alcohols, ketones, and polyalkylene glycol ethers and esters can be used in conjunction with these petroleum solvents.

Compositions of the present invention can also be formulated as emulsifiable concentrates which are concentrated solutions or dispersion of the active ingredient in an organic liquid, preferably a water-insoluble organic liquid, containing an added emulsifying agent. These concentrates can also contain a proportion of water, for example, up to about 50% by volume, based on the total composition, to facilitate subsequent dilution with water. Suitable organic liquids include, e.g. the above petroleum hydrocarbon fractions previously described.

The emulsifying agent can be of the type producing water-in-oil type emulsions which are suitable for application by low volume spraying, or an emulsifier of the type producing oil-in-water emulsions can be used, producing concentrates which can be diluted with relatively large volumes of water for application by high volume spraying or relatively small volumes of water for low volume spraying. In such emulsions, the active ingredient is preferably in an nonaqueous phase.

The present invention is further illustrated in greater detail by the following examples, but it is to be understood that the present invention in its broadest aspects, is not necessarily limited in terms of the reactants, or specific temperatures, residence times, separation techniques and other process conditions, etc.; or dosage level, exposure times, test plants used, etc. by which the compounds and/or compositions described and claimed are prepared and/or used.

EXAMPLE 1

Preparation of 4-Chloromethyl 2,2-Dimethyl 1,3-Dithiolane

Acetone (19 g. 0.33 mole) and 40 g. (0.33 mole) of 2,3-dimercaptopropanol were dissolved in 100 ml. of benzene. Hydrogen chloride was bubbled into the solution which caused a temperature rise to 44°C. The hydrogen chloride was bubbled in for an additional 2 hours after which the benzene solution was washed with 500 ml. of water. The benzene solution was dried over anhydrous magnesium sulfate and the solvent was removed under vacuum to yield 44.5 g. (79%) of 4-chloromethyl 2,2-dimethyl 1,3-dithiolane. Structure elucidation was carried out by nuclear magnetic resonance (nmr) spectroscopy.

EXAMPLE 2

O,O-diethyl-S-[(2,2-dimethyl-1,3-dithiolan-4-yl)-methyl]-phosphorothioate.

4-chloromethyl 2,2-dimethyl 1,3-dithiolane (36.5 g. 0.2 mole) and 31.8 g (0.2 mole) of ammonium O,O-dimethyl phosphorothioate were dissolved in 500 ml. of acetonitrile and stirred for 60 hours at ambient temperature. A white precipitate formed which was removed by filtration. The filtrate was concentrated under vacuum, dissolved in ether and washed with water. The ethereal solution was dried over $MgSO_4$ and solvent was removed under vacuum to yield 40 g. (70%) of the desired product. Structure was elucidated by nmr spectroscopy.

EXAMPLE 3

O,O-dimethyl-S-[(2,2-dimethyl-1,3-dithiolan-4-yl)-methyl]phosphorodithioate

4-Chloromethyl 2,2-dimethyl 1,3-dithiolane (7.8 g., 0.05 mole) and 9.7 g. (0.05 mole) of potassium O,O-dimethyl phosphorodithionate were dissolved in 100 ml. of acetonitrile and the solution was refluxed for 12 hours. The work-up of the reaction was carried out according to Example 2 to yield 7.3 g. (50%) of desired product as shown by nmr spectroscopy.

EXAMPLE 4

O,O-diethyl-S-[(2,2-dimethyl-1,3-dithiolan-4-yl)-methyl]phosphorothioate

4-Chloromethyl 2,2-dimethyl 1,3-dithiolane (7.8 g., 0.05 mole) and 9.4 g. (0.05 mole) of ammonium O,O-diethyl phosphorothioate were reacted according to the procedure of Example 3 to yield 7.7 g. (50%) of the desired product as shown by nmr spectroscopy.

EXAMPLE 5

O,O-diethyl-S-[(2,2-dimethyl-1,3-dithiolan-4-yl)-methyl]phosphorodithioate

According to the procedure of Example 3, 7.8 g. (0.05 mole) of 4-chloromethyl 2,2-dimethyl 1,3-dithiolane and 10.2 g. (0.05 mole) of ammonium O,O-diethyl phosphorodithioate were reacted to yield 12.3 g. (74%) of the desired product as shown by nmr spectroscopy.

EXAMPLE 6

O-ethyl-S-1-propyl-S'-[(2,2-dimethyl-1,3-dithiolan-4-yl)-methyl]phosphorodithioate According to the procedure of Example 3, 7.8 g. (0.05 mole) of 4-chloromethyl 2,2-dimethyl 1,3-dithiolane and 11.9 g. (0.05 mole) of potassium O-ethyl S-1-propyl phosphorodithioate were reacted to yield 9.5 g. (55%) of the desired product as shown by nmr spectroscopy.

EXAMPLE 7

Preparation of 4-Hydroxymethyl 2-Phenyl 1,3-Dithiolane

According to the procedure of Example 1, 35 g. (0.33 mole) of benzaldehyde and 40 g. (0.33 mole) of 2,3-dimercaptopropanol were reacted to yield 63.6 g. of crude product. After recrystallization 42.4 (56%) of the desired product were obtained as shown by nmr spectroscopy.

EXAMPLE 8

Preparation of 4-Bromomethyl 2-Phenyl 1,3-Dithiolane

4-Hydroxymethyl 2-phenyl 1,3-dithiolane (30 g., 0.14 mole) was suspended in 150 ml of ether and cooled to 0°C. Phosphorus tribromide (15 g., 0.053 mole) were added over a 1.5 hour period and the mixture was stirred at ambient temperature with 5% aqueous $NaHCO_3$ until neutral (ph = 7). After drying over $MgSO_4$ the solvent was removed under vacuum to yield 38 g. (99%) of desired product.

Analysis: Calculated for $C_{10}H_{11}Br\ S_2$: C, 43.6; H, 4.0; S, 23.2 Found: C, 43.8; H, 3.8; S, 23.6

EXAMPLE 9

O,O-diethyl-S-[(2-phenyl-1,3-dithiolan-4-yl)-methyl]phosphorothioate

According to the procedure of Example 3, 13.8 g. (0.05 mole) of 4-bromomethyl 2-phenyl 1,3-dithiolane and 9.4 g. (0.05 mole) of ammonium O,O-diethyl phosphorothioate were reacted to yield 14.5 g. of the desired product as shown by nmr spectroscopy.

Analyses: Calculated for $C_{14}H_{21}O_3P\ S_3$; C, 46.2; H, 5.67; P, 8.52; S, 26.4. Found: C, 45.0: H, 5.77; P, 8.27; S, 26.2.

EXAMPLE 10

O-ethyl-S-1-propyl-S'[(2-phenyl-1,3-dithiolan-4-yl)-methyl]phosphorodithioate

According to the procedure of Example 3, 13.8 g. (0.05 mole) of 4-bromomethyl 2-phenyl 1,3-dithiolane and 11.9 g. (0.05 mole) of potassium O-ethyl S-1-propyl phosphorodithioate were reacted to give 15.1 g. (83%) of the desired product as shown by nmr spectroscopy.

Analyses: Calculated for $C_{15}H_{23}O_2\ P\ S_4$: C, 47.6; H, 6.09; P, 8.20; S, 33.9. Found: C, 45.1; H, 5.92; P, 7.91; S, 31.9.

EXAMPLE 11

Preparation of 4-Hydroxymethyl 2,2-Spirocyclopentyl 1,3-Dithiolane

According to the procedure of Example 1, 27.8 g. (0.33 mole) of cyclopentanone and 40 g. (0.33 mole) of 2,3-dimercaptopropanol were reacted to yield 55 g. (87%) of the desired product as shown by nmr spectroscopy,

EXAMPLE 12

Preparation of 4-Bromomethyl 2,2-Spirocyclopentyl 1,3-Dithiolane

According to the procedure of Example 8, 55 g. (0.29 mole) of 4-hydroxymethyl 2-spirocyclopentyl 1,3-dithiolane and 27.5 g. of phosphorus tribromide were reacted to yield 64.5 g. (88%) of the desired product as shown by nmr spectroscopy.

Analyses: Calculated for $C_8H_{13}Br\ S_2$: C, 38.0; H, 5.17. Found: C, 38.4; H, 5.12

Example 13

O,O-dimethyl-S-[(2,2-spirocyclopentyl-1,3-dithiolan-4-yl)-methyl]phosphorothioate.

According to the procedure of Example 3, 17.7 g. (0.07 mole) of 4-bromomethyl 2,2-spirocyclopentyl 1,3-dithiolane and 12.6 g. (0.07 mole) of potassium O,O-dimethyl phosphorothioate were reacted to yield 19.5 g. (89%) of desired product as shown by nmr spectroscopy.

Analyses: Calculated for $C_{10}H_{19}O_3PS_3$: C, 38.3; H, 6.03; P, 9.87; S, 30.5. Found: C, 38.9; H, 6.27; P, 9.34; S, 31.0.

EXAMPLE 14

O,O-diethyl-S-[(2,2-spirocyclopentyl-1,3-dithiolan-4-yl)-methyl]phosphorothioate.

According to the procedure of Example 3, 17.7 g. (0.07 mole) of 4-bromomethyl 2,2-spirocyclopentyl-1,3-dithiolane and 13.1 g. of ammonium 0,0-diethyl-phosphorothioate were reacted to yield 32.5 g. (94%) of the desired product as shown by nmr spectroscopy.

Analyses: Calculated for $C_{12}H_{23}O_3PS_3$: C, 42.2; H, 6.73; P, 9.06; S, 28.1. Found: C, 42.6; H, 6.87; P, 8.79; S, 28.6.

EXAMPLE 15

O-ethyl-S-1-propyl-S'-[(2,2-spirocyclopentyl-1,3-dithiolan-4-yl)-methyl]phosphorodithioate According to the procedure of Example 3, 17.7 g. (0.07 mole) of 4-bromomethyl 2,2- spirocyclopentyl-1,3-dithiolane were reacted to yield 17.2 g. (65%) of the desired product as shown by nmr spectroscopy.

Analyses: Calculated for $C_{13}H_{25}O_2PS_4$: C, 42.1: H, 6.72; P, 8.33; S, 34.2. Found: C, 42.3; H, 7.06; P, 8.20; S, 34.4.

EXAMPLE 16

General Experimental Procedures for Biological Testing

In the examples which follow, the new organophosphorus derivatives of 1,3-dithiolanes were treated in the greenhouse and in the laboratory to determine their biological activity.

The experimental compounds were tested as aqueous emulsions. These emulsions were prepared by dissolving the compound in acetone and dispersing it in distilled water with Triton X-100, an alkylaryl polyether alcohol derived by the reaction of i-octyl phenol with ethylene oxide, to give spray emulsions containing the desired concentration of the compound. These emulsions were then used in standard laboratory tests described below.

Mexican Bean Beetle: Bean leaves were dipped in the emulsion of the test chemical and allowed to dry. The individual treated leaves were placed in Petri dishes and five Mexican bean beetle larvae introduced into each of the two replicate dishes.

Mites, Contact: Potted bean plants infested with the twospotted spider mites were placed on a turntable and sprayed with a formulation of the test chemical. The plants were held for seven days and the degree of mite control was rated after this period.

Mites, Systemic: Bean plants were treated by applying 20 ml. of the formulated test chemical to the soil. The mites were transferred to the plants after 24 hours. The plants were held for seven more days and the degree of mite control rated.

Aphid, Contact: Potted nasturtium plants infested with the bean aphids were placed on a turntable and sprayed with a formulation of the test chemical. The plants were held for two days and the degree of aphid control was rated.

Aphid, Systemic: Nasturtium plants were treated by applying 20 ml. of the formulated test chemical to the soil. The mites were transferred to the plants after 24 hours. The plants were held for 48 additional hours and the degree of the Aphid control rated.

Southern Army Worm: Bean leaves were dipped in the emulsion of the test chemical of desired concentration and allowed to dry. The individual treated leaves were placed in Petri dishes and five Southern ArmyLarvae introduced into each of the two replicate dishes. The plants were held for two days and the degree of control was rated.

Some of the compounds were also tested against other species of coleoptera family such as confused flour beetle and spider beetle, as well as adult Mexican bean beetles. They were also tested for their effectiveness to control German cockroaches. Tests were also done to determine their ovicidal action, and were active against one or more of these species.

Representative data for a number of compounds demonstrating their insecticidal activity are presented in Tables I, II and III.

TABLE I

INSECTICIDAL ACTIVITY OF ORGANOPHOSPHATE DERIVATIVES OF 2,2-DIMETHYL 1,3-DITHIOLANE

| Experimental Compounds | Conc. (ppm) | Mexican Bean Beetle | S.Army Worm | Mites Cont. | Mites Syst. | Aphids Cont. | Aphids Syst. |
|---|---|---|---|---|---|---|---|
| O,O-dimethyl-S-[(2,2-dimethyl-1,3-dithiolan-4-yl)-methyl]-phosphorothioate | 250 | 100 | 0 | 100 | 100 | 60 | 100 |
|  | 50 | 100 |  | 100 | 100 |  |  |

TABLE I-continued
INSECTICIDAL ACTIVITY OF ORGANOPHOSPHATE DERIVATIVES OF 2,2-DIMETHYL 1,3-DITHIOLANE

| Experimental Compounds | Conc. (ppm) | % Mortality | | | | | |
|---|---|---|---|---|---|---|---|
| | | Mexican Bean Beetle | S.Army Worm | Mites Cont. | Mites Syst. | Aphids Cont. | Aphids Syst. |
| O,O-dimethyl-S-[(2,2-dimethyl-1,3-dithiolan-4-yl)-methyl]-phosphorodithioate | 250 | 100 | 0 | 100 | 100 | 95 | 90 |
| | 50 | 80 | | 100 | 90 | 90 | 15 |
| O,O-diethyl-S-[(2,2-dimethyl-1,3-dithiolan-4-yl)-methyl]-phosphorothioate | 250 | 100 | 0 | 100 | 100 | 90 | 70 |
| | 50 | 100 | | 95 | 100 | 90 | 0 |
| O,O-diethyl-S-[(2,2-dimethyl-1,3-dithiolan-4-yl)-methyl]-phosphorodithioate | 250 | 100 | 0 | 95 | 75 | 70 | 40 |
| | 50 | 0 | | 80 | 30 | | |
| O-ethyl-S-1-propyl-S'-[(2,2-dimethyl-1,3-dithiolan-4-yl)-methyl]-phosphorodithioate | 250 | 100 | 100 | 75 | 70 | 50 | 50 |
| | 50 | 90 | 75 | 25 | 40 | | |

TABLE II
INSECTICIDAL ACTIVITY OF ORGANOPHOSPHATE DERIVATIVES OF 2-PHENYL 1,3-DITHIOLANE

| Experimental Compounds | Conc. (ppm) | % Mortality | | | | | |
|---|---|---|---|---|---|---|---|
| | | Mexican Bean Beetle | S.Army Worm | Mites Cont. | Mites Syst. | Aphids Cont. | Aphids Syst. |
| O,O-diethyl-S-[(2-phenyl-1,3-dithiolan-4-yl)-methyl]-phosphorothioate | 250 | 100 | 0 | 100 | 0 | 100 | 20 |
| | 50 | 100 | | 100 | | 25 | 0 |
| O-ethyl-S-1-propyl-S'-[(2-phenyl-1,3-dithiolan-4-yl)-methylphosphorodithioate | 250 | 100 | 100 | 100 | 0 | 80 | 20 |
| | 50 | 100 | 70 | 100 | | 80 | 10 |

TABLE III
INSECTICIDAL ACTIVITY OF ORGANOPHOSPHATES DERIVATIVES OF 2,2-SPIROCYCLOPENTYL 1,3-DITHIOLANE

| Experimental Compound | Conc. (ppm) | % Mortality | | | | | |
|---|---|---|---|---|---|---|---|
| | | Mexican Bean Beetle | S.Army Worm | Mites Cont. | Mites Syst. | Aphids Cont. | Aphids Syst. |
| O,O-dimethyl-S-[(2,2-spirocyclopentyl-1,3-dithiolan-4-yl)-methyl]-phosphorothioate | 250 | 100 | 0 | 100 | 100 | 100 | 26 |
| | 50 | 100 | | 100 | 100 | 85 | 10 |
| O,O-diethyl-S-[(2,2-spirocyclopentyl-1,3-dithiolan-4-yl)-methyl]-phosphorothioate | 250 | 100 | 0 | 70 | 95 | 90 | 0 |
| | 50 | 100 | | | 65 | 60 | |
| O-ethyl-S-1-propyl-S'-[(2,2-spirocyclopentyl-1,3-dithiolan-4-yl)-methyl]-phosphorodithioate | 250 | 100 | 100 | 100 | 30 | 85 | 0 |
| | 50 | 100 | 100 | 100 | | 40 | |

I claim:

1. O-Ethyl-S-1-propyl-S'-[(2,2-dimethyl-1,3-dithiolan-4-yl)-methyl]-phosphorodithioate.

2. O-Ethyl-S-1-propyl-S'-[(2-phenyl-1,3-dithiolan-4-yl)-methyl]-phosphorodithioate.

3. O-Ethyl-S-1-propyl-S'-[(2,2-spirocyclopentyl-1,3-dithiolan-4-yl)-methyl]-phosphorodithioate.

* * * * *